United States Patent
Re et al.

(10) Patent No.: US 6,645,944 B2
(45) Date of Patent: *Nov. 11, 2003

(54) INHIBITION OF CELLULAR PROLIFERATION BY OLIGONUCLEOTIDE BINDING TO A CHROMOSOMAL BINDING SITE FOR P53 PROTEIN

(75) Inventors: Richard Re, Metairie, LA (US); Julia Cook, Kenner, LA (US)

(73) Assignee: Alton Ochsner Medical Foundation, New Orleans, LA (US)

( * ) Notice: Subject to any disclaimer, the term of this patent is extended or adjusted under 35 U.S.C. 154(b) by 5 days.

This patent is subject to a terminal disclaimer.

(21) Appl. No.: 09/935,247

(22) Filed: Aug. 22, 2001

(65) Prior Publication Data

US 2002/0103153 A1 Aug. 1, 2002

Related U.S. Application Data

(63) Continuation of application No. 09/266,065, filed on Mar. 10, 1999, now Pat. No. 6,303,328, which is a continuation of application No. 08/291,011, filed on Aug. 15, 1994, now Pat. No. 5,936,079, which is a continuation of application No. 07/879,618, filed on May 1, 1992, now abandoned, which is a continuation-in-part of application No. 07/863,661, filed on Apr. 6, 1992, now abandoned.

(51) Int. Cl.[7] .................. A01N 43/04; A61K 31/70; C12Q 1/02; C07H 21/04
(52) U.S. Cl. .................. 514/44; 435/29; 435/455; 536/24.5
(58) Field of Search .................. 514/44; 435/29, 435/455; 536/24.5

(56) References Cited

U.S. PATENT DOCUMENTS

| | | |
|---|---|---|
| 5,087,617 A | 2/1992 | Smith |
| 5,098,890 A | 3/1992 | Gewirtz et al. |
| 5,585,479 A | 12/1996 | Hoke et al. |

OTHER PUBLICATIONS

Stein et al. Antisense Oligonucleotides as Therapeutic Agents—Is the Bullet Really Magical? Science. Aug. 20, 1993, vol. 261, pp. 1004–1012.*

Tseng et al. Antisense Oligonucleotide Technology in the Development of Cancer Therapeutics. Cancer Gene Therapy. 1994, vol. 1, No. 1, pps 65–71.*

Wu–Pong. Oligonucletodies: Opportunities for Drug Research. Pharmacology Today. Oct. 1994, pps 102–114.*

Ben–David et al. (1991) "Friend Virus–Induced Erythroleukemia and the Multistage Nature of Cancer", *Cell* 66:831–834.

Bennett (1996) *Science* 271:1134.

Brysch et al. (1994) *Cell and Mol. Neurobiol.* 14(5):557–568.

Cooney et al. (1988) "Site–Specific Oligonucleotide Binding Represses Transcription of the Human c–*myc* Gene In Vitro", *Science* 241:456–459.

Crook et al. (1991) *Cell* 67: 547–556.

Finlay et al. (1989) "The p53 Proto–Oncogene can Act as a Suppressor of Transformation", *Cell* 57:1083–1093.

Friedmann (1992) *Cancer (Supp.)* 70(6):1810–1816.

Gewirtz et al. (1996) *Proc Nat. Acad. Sci.* 93:3161–3163.

Goodchild et al. (1988) "Inhibition of Human Immunodeficiency Virus Replilcation by Antisense Oligodeoxynucleotides", *Proc. Natl. Acad. Sci. USA* 85:5507–5511.

Haber et al. (1991) Rate–Limiting Steps: The Genetics of Pediatric Cancer, *Cell* 64:5–8.

Hara et al. (1991) *Biochem. Biophys. Res. Comm.* 179(1):528–534.

Iguchi–Ariga et al. (1988) *Oncogene* 3:509–515.

Kern et al. (1991) "Identification of p53 as a Sequence–Specific DNA–Binding Protein", *Science* 252:1708–1711.

Kern et al. (1991) "Mutant p53 Proteins Bind DNA Abnormally in vitro", *Oncogene* 6:131–136.

Maher et al. (1989) "Inhibition of DNA Binding Proteins by Oligonucleotide–Directed Triple Helix Formation", *Science* 245:725–730.

Miller et al. (1994) *Parasitology Today* 10(3):92–97.

Riordan et al. (1991) "Oligonucleotide–Based Therapeutics", *Nature* 350:442–443.

Rojanasakul (1996) *Adv. Drug. Del. Rev.* 18:115–131.

Stall et al. (1995) *Pharm. Res.* 12(4):465–483.

Stein et al. (1993) *Science* 261:1004–1012.

Uhlmann et al. (1990) *Chem. Reviews* 90(4):544–584.

Wu–Pong (1994) *Pharmaceutical Tech.* 18:102–114.

* cited by examiner

Primary Examiner—Deborah Crouch
(74) Attorney, Agent, or Firm—Scully, Scott, Murphy & Presser

(57) ABSTRACT

The present invention provides methods for inhibiting cell growth by providing a growing cell with an oligonucleotide capable of binding to a chromosomal binding site for p53 protein. Moreover, in a preferred embodiment these methods can be used for preventing and treating cancer.

32 Claims, No Drawings

INHIBITION OF CELLULAR PROLIFERATION BY OLIGONUCLEOTIDE BINDING TO A CHROMOSOMAL BINDING SITE FOR P53 PROTEIN

CROSS-REFERENCE TO RELATED APPLICATIONS

This application is a continuation of Ser. No. 09/266,065, filed on Mar. 10, 1999 now U.S. Pat. No. 6,303,328 B1 issued Oct. 16, 2001, which is a continuation of Ser. No. 08/291,011, filed on Aug. 15, 1994 now U.S. Pat. No. 5,936,079 issued on Aug. 10, 1999, which is a continuation of Ser. No. 07/879,618, filed on May 1, 1992 (now abandoned), which is a continuation-in-part of Ser. No. 07/863,661, filed on Apr. 6, 1992 (now abandoned).

FIELD OF THE INVENTION

The present invention relates to methods for inhibiting mammalian cellular replication. In a preferred embodiment, cell growth is inhibited in mammals for prevention and treatment of cancer. According to the present invention, cell growth is inhibited by binding of oligonucleotides to chromosomal sites normally bound by proteins, e.g. the p53 protein, whose normal function is to suppress uncontrolled cell division.

BACKGROUND OF THE INVENTION

The process by which cellular replication occurs is complex, involving many steps and numerous factors including regulatory, cytoskeletal and polymerization proteins. However, some early steps in this complex process are known to be essential, for example, initiation of DNA replication.

In higher eukaryotes, DNA replication is thought to be initiated at many origins of replication present on chromosomal DNA. By virtue of homology to known viral origins of replication, some highly repeated eukaryotic origins of replication have been identified and sequenced (Jelinek et al. 1980 *Proc. Natl. Acad. Sci. USA* 77: 1398–1402).

Moreover some proteins have been identified which have a role in regulation of cell growth. For example many of the cellular protooncogenes are thought to have a normal role in cellular replication which is improperly executed when the protooncogene becomes mutated. The p53 gene is such a protooncogene. Normally the p53 protein appears to inhibit cell growth, however mutant p53 proteins can have an opposite effect upon cell growth, causing uncontrolled cell division and a variety of cancers, especially sarcomas, breast, brain, adrenal cortex, colon, lung and leukemic cancers (Finlay et al. 1989 *Cell* 57: 1083–1093; Ben-David et al. 1991 *Cell* 66: 831–834; and Haber et al. 1991 *Cell* 64: 5–8). Moreover, the p53 protein binds to DNA sites in a sequence-specific manner (Kern et al. 1991a *Science* 252: 1708–1711; Kern et al. 1991b *Oncogene* 6: 131–136). However, the significance of DNA binding by p53 protein relative to the role of p53 protein in cellular replication has not been established.

According to the present invention, cell growth is inhibited by site-specific oligonucleotide binding to DNA. Specifically, the site to which the oligonucleotide binds is a DNA site which can be bound by a protein repressor of cellular replication, e.g. the p53 protein.

Oligonucleotides have recently attracted attention as regulators of nucleic acid biological function. Naturally occurring complementary, or antisense, RNA are used by some cells to control protein expression or plasmid replication. For example, replication of some *Escherichia coli* plasmids, including the ColE1 plasmid, is regulated by an antisense RNA complementary to an RNA primer of ColE1 DNA replication (Lacatena et al. 1981 *Nature* 294: 623–626; Lin-Chao et al. 1991 *Cell* 65: 1233–1242).

Specific oligonucleotides have also been synthesized and tested as inhibitors of nucleic acid function. For example, splicing of a pre-mRNA transcript essential for Herpes Simplex virus replication has been inhibited with a linear oligonucleotide complementary to an acceptor splice junction (Smith et al., 1986, *Proc. Natl. Acad. Sci. USA* 83: 2787–2791). A linear oligonucleotide has also been used to inhibit protein synthesis of a human immunodeficiency virus (HIV) p24 protein (Agrawal et al. 1988 *Proc. Natl. Acad. Sci. USA* 85: 7079–7083). In another example, linear oligonucleotides were used to inhibit HIV replication in cultured cells. Linear oligonucleotides complementary to sites within or near the terminal repeats of the HIV retroviral genome and within sites complementary to certain splice junctions were most effective in blocking viral replication (Goodchild et al., 1988, *Proc. Natl. Acad. Sci. USA* 85: 5507–5511). Accordingly, the use of oligonucleotides as inhibitors of nucleic acid function has been limited to inhibition of functions such as RNA splicing, protein translation and viral replication via formation of Watson-Crick base pairs between an oligonucleotide and a nucleic acid template. The inhibition of cell growth by oligonucleotide binding has not been demonstrated.

An oligonucleotide binds to a target nucleic acid by forming hydrogen bonds between bases in the target and the oligonucleotide. Common B DNA has conventional adenine-thymine (A-T) and guanine-cytosine (G-C) Watson and Crick base pairs with two and three hydrogen bonds, respectively. The most common bonds that form between two complementary strands of RNA or DNA are Watson-Crick hydrogen bonds. However, other types of hydrogen bonding patterns are known wherein some atoms of a base which are not involved in Watson-Crick base pairing can form hydrogen bonds to another, third, nucleotide. For example, thymine (T) can bind to an A-T Watson-Crick base pair via hydrogen bonds to the adenine, thereby forming a T-AT base triad. Hoogsteen (1959, Acta Crystallography 12: 822) first described the alternate hydrogen bonds present in T-AT and C-GC base triads. More recently, G-TA base triads, wherein guanine can hydrogen bond with a central thymine, have been observed (Griffin et al., 1989, *Science* 245: 967–971).

Oligonucleotides have also been observed to bind and inhibit the function of a nucleic acid through non-Watson-Crick hydrogen bonding. For example, Cooney et al. (1988, *Science* 241: 456) disclose a 27-base single-stranded oligonucleotide which bound to a double-stranded nucleic acid via non-Watson-Crick hydrogen bonds. This oligonucleotide inhibited transcription of the human c-myc gene in a cell free, in vitro assay by binding to the c-myc promoter. In a review, Riordan et al. suggest that linear "switchback" oligonucleotides can be used to bind and inhibit the function of both strands of a double stranded nucleic acid target by Watson-Crick binding to one target strand and non-Watson-Crick binding to the other target strand (Riordan et al. 1991 *Nature* 350: 442–443. However, methods for inhibiting cell growth by either non-Watson-Crick or Watson-Crick binding of an oligonucleotide to a chromosomal binding site for a protein repressor of cellular replication are not available in the prior art.

Accordingly, the present invention represents an innovative step forward in the technology of cell cycle control by providing methods for inhibiting cellular replication through Watson-Crick and non-Watson-Crick binding of an oligonucleotide to chromosomal sites normally bound by protein repressors of cellular replication.

SUMMARY OF THE INVENTION

The present invention is directed to a method for inhibiting mammalian cell growth by providing a growing mammalian cell with a cell growth-inhibiting amount of an oligonucleotide comprising an RNA or a DNA which binds to a chromosomal binding site for p53 protein and thereby inhibiting said mammalian cell growth.

An additional aspect of the present invention provides a method of preventing or treating cancer by administering to a patient a therapeutically effective amount of an oligonucleotide comprising an RNA or a DNA which binds to a chromosomal binding site for p53 protein.

Another aspect of the present invention provides methods for inhibiting in vitro mammalian cell growth by contacting cultured mammalian cells with a cell growth inhibiting amount of an oligonucleotide comprising an RNA or a DNA which binds to a chromosomal binding site for p53 protein and thereby inhibiting said in vitro mammalian cell growth.

A further aspect of this invention is directed to a method of inhibiting cell growth in a mammal or a cultured mammalian cell by binding one of the present oligonucleotides to a chromosomal site for p53 protein either by Watson-Crick or non-Watson-Crick base pairs to form a double-helical or a triple-helical oligonucleotide-DNA complex, respectively.

Yet another aspect of the present invention provides a composition which includes a therapeutically effective amount of an oligonucleotide which can bind to a chromosomal binding site for p53 protein and a pharmaceutically acceptable carrier.

DETAILED DESCRIPTION OF THE INVENTION

This invention relates to inhibition of cellular growth by oligonucleotides capable of binding to chromosomal sites normally bound by protein repressors of cell replication. Moreover, the present invention contemplates inhibition of cellular replication in mammals for the treatment and prevention of cancer as well as inhibition of cultured cell replication.

In particular, the present invention provides a method for inhibiting mammalian cell growth by providing growing cells with a cell growth-inhibiting amount of an oligonucleotide which can be an RNA or a DNA capable of binding to a chromosomal binding site for p53 protein, and thereby inhibiting mammalian cell growth. Moreover, according to the present invention, cell growth is preferably inhibited to treat or prevent cancer. In particular, this invention includes a method for preventing or treating cancer by administering to a patient a therapeutically effective amount of an oligonucleotide which can be an RNA or a DNA which binds to a chromosomal binding site for p53 protein.

In another embodiment, the present invention provides a method for inhibiting in vitro mammalian cell growth by contacting cultured mammalian cells with a cell growth-inhibiting amount of an oligonucleotide which is an RNA or a DNA capable of binding to a chromosomal binding site for p53 protein, and thereby inhibiting in vitro mammalian cell growth.

A sequence for a chromosomal binding site for p53 protein is known (Kern et al. 1991 *Science* 252: 1708–1711) and has been designated herein as a portion of SEQ ID NO:1. The sequence of SEQ ID NO:1, is depicted below:

```
5'-TAAGCTTGATATTCTCCCCAGATGTAGTGAAAGCAGGTAGATTGCCTTGCC
3'-ATTCGAACTATAAGAGGGGTCTACATCACTTTCGTCCATCTAACGGAACGG

TGGACTTGCCTGGCCTTGCCTTTTCTTTCTTTCTTTCTTTCTTTATTACTTTCT
ACCTGAACGGACCGGAACGGAAAAGAAAGAAAGAAAGAAAGAAATAATGAAAGA

CTTTTTCTTCTTCTTCTTCTTCTTCTTCTTCTTCTTCTTCTTCTTCTTCTTCTT
GAAAAAGAAGAAGAAGAAGAAGAAGAAGAAGAAGAAGAAGAAGAAGAAGAAGAA

CTTCTTCTTCTTTTTTTTTTGAGACAGAG-3'
GAAGAAGAAGAAAAAAAAAACTCTGTCTC-5'.
```

Portions of SEQ ID NO:1 which can be chromosomal binding sites for p53 protein include, but are not limited to, SEQ ID NO:2–5, SEQ ID NO:7–9 and SEQ ID NO:13. SEQ ID NO:2 and 3 correspond to positions 56–83 of SEQ ID NO:1, while SEQ ID NO:4 and 5 correspond to positions 61–96 of SEQ ID NO:1. SEQ ID NO:7–9 correspond to positions 43–71, 70–95 and 100–121 of SEQ ID NO:1, respectively. SEQ ID NO:13 corresponds to positions 60–83 of SEQ ID NO:1. The sequences of SEQ ID NO:2–5, 7–9 and 13 are depicted below:

SEQ ID NO:2:   5'-CTTGCCTGGACTTGCCTGGCCTTGCCTTTTCTTTCTTT;

SEQ ID NO:3:   5'-AAAGAAAGAAAAGGCAAGGCCAGGCAAGTCCAGGCAAG;

SEQ ID NO:4:   5'-CTGGCCTTGCCTTTTCTTTCTTTCTTTCTTTCTTTA;

SEQ ID NO:5:   5'-TAAAGAAAGAAAGAAAGAAAGAAAAGGCAAGGCCAG;

SEQ ID NO:7:   5'-TGCCTTGCCTGGACTTGCCTGGCCTTGCC-3'
               3'-ACGGAACGGACCTGAACGGACCGGAACGG-5';

SEQ ID NO:8:   5'-TTTCTTTCTTTCTTTCTTTCTTTTCC;

SEQ ID NO:9:   5'-CTTCTTCTTCTTTTTCTCTTTC; and

SEQ ID NO:13:  5'-TTTCTTTCTTTTCCGTTCCGGTCC-3'
               3'-AAAGAAAGAAAAGGCAAGGCCAGG-5'.

According to the present invention a chromosomal binding site for p53 protein is a domain within a chromosomal DNA having sufficient homology to a nucleotide sequence corresponding to either or both strands of SEQ ID NO:1, or a portion thereof, to permit detectable binding by p53 protein. The size of chromosomal site for p53 protein can be about 10 to about 200 bases or base pairs and is preferably about 10 to about 50 bases or base pairs.

Binding of p53 protein to a chromosomal DNA can be detected by any procedure available in the art, for example by immunoprecipitation, gel shift, DNA footprinting, methylation interference and similar assays, for example, as provided in Finlay et al. (1989 Cell 57: 1083–1093), Kern et al. (1991 *Science* 252: 1708–1711) and Sambrook et al. (1989, *Molecular Cloning: A Laboratory Manual,* Vols. 1–3, Cold Spring Harbor Press, NY). Moreover, recombinant p53 protein is available and can be obtained as a pure or semi-pure preparation (Friedman et al. 1990 *Proc. Natl. Acad. Sci. USA* 87: 9275; Hinds et al. 1989 *J. Virol.* 63: 739–746; Finlay et al. 1989 *Cell* 57: 1083–1093). Furthermore, anti-p53 antibodies and kits for detection of p53 protein can be obtained commercially (Oncogene Sciences, Uniondale, N.Y.). Accordingly one of skill in the art can readily utilize procedures and commercially available materials to determine whether p53 protein binds to a DNA having a given sequence, and thereby ascertain the degree of homology to SEQ ID NO:1 required by a chromosomal site to permit binding by p53 protein.

In a preferred embodiment, chromosomal DNA sites having greater than about 50%, and preferably greater than about 70%, homology to a portion of SEQ ID NO:1 are sufficiently homologous to be chromosomal sites permitting binding by p53 protein. Moreover, in an especially preferred embodiment, chromosomal sites are selected which can detectably bind at least 50% or more of the p53 protein bound by a DNA having SEQ ID NO:1–4, SEQ ID NO:7–9 or SEQ ID NO:13.

According to the present invention a patient is a human. Moreover a mammalian cell is an animal cell having a chromosomal DNA which encodes one or more copies of a binding site for p53 protein. Preferred mammalian cells are human, ape, monkey, mouse, rat, hamster, rabbit, cat, dog, horse, sheep, cow, bull and similar mammalian cells. Especially preferred mammalian cells of the present invention are human, monkey, mouse, rat and hamster cells.

Proliferation can be inhibited in numerous cells within a mammal, e.g., to prevent or treat cancer, by the methods of the present invention. In particular, this invention has utility for inhibiting growth of any cell type which can have a mutant or absent p53 protein or which can become cancerous when the p53 gene becomes mutated or is absent.

For example, according to the present invention, epithelial, mesothelial or endothelial cell growth can be inhibited in a mammal. Moreover, such cell types can be cancerous or non-cancerous mesangial, embryonic, brain, lung, breast, uterine, cervical, ovarian, prostate, adrenal cortex, skin, blood, brain, bladder, gastrointestinal, colon and related cells. In a preferred embodiment cellular proliferation can be inhibited in a mammal for treatment of a cancer. As used herein a cancer can be a carcinoma, sarcoma, breast, brain, adrenal cortex, colon, bladder, prostate, lung, leukemic or a related cancer.

According to the present invention, a mammalian cell having a mutant or absent p53 protein, or a mutant or absent p53 gene, can be identified by any known procedure, including by immunological, sequencing or hybridization procedures. For example, cells expressing mutant p53 protein can be distinguished from cells expressing wild type p53 protein by commercially available antibodies which can distinguish between these proteins (oncogene Science). Moreover, labeled nucleic acid probes homologous to genomic DNA encoding p53 protein can be used to identify changes in p53 mRNA or p53 DNA restriction fragment size by standard hybridization procedures (Sambrook et al.).

As used herein in vitro mammalian cellular proliferation means mammalian cell growth in culture. Moreover, mammalian cells whose proliferation can be inhibited in vitro by the methods of the present invention include any primary or immortalized cell line having a chromosomal DNA which encodes a binding site for p53 protein.

As used herein primary cell lines include cancerous and non-cancerous cells derived from any mammalian tissue specimen, for example, from mesangial, embryonic, brain, lung, breast, uterine, cervical, ovarian, prostate, adrenal cortex, skin, blood, brain, bladder, gastrointestinal, colon and related tissues. Immortalized cell lines can include human HeLa, colon 201, neuroblastoma, retinoblastoma and KB cell lines, mouse 3T3, L and MPC cell lines, hamster CHO and BHK 21 cell lines, a monkey BSC cell line and other cell types, for example mammalian cell types available from the American Type Culture Collection.

According to the present invention, cell growth is inhibited by binding one or more of the subject oligonucleotides to a p53 protein chromosomal binding site. Binding of the oligonucleotide has a similar effect upon cell growth as wild type p53 protein binding, i.e. inhibition of cell growth. Moreover, the methods of the present invention have been used to inhibit cell growth by up to 85%.

Without limiting the invention, binding of the present oligonucleotides may block access to that chromosomal binding site. Blocking access to this site can prevent factors, e.g. nucleic acids or proteins, involved in cellular or DNA replication from binding to or recognizing the chromosome at this site, from dissociating the two strands of chromosomal DNA at this site, from moving along the chromosome, or from recognizing signals encoded within the chromosome at this site. Therefore, blocking access to the chromosomal binding site for p53 protein may inhibit normal processes essential for cellular or DNA replication and thereby may inhibit cell growth.

Inhibition of cell growth by the present oligonucleotides can be observed in vitro or in vivo by any procedure available in the art. For example, in vitro inhibition can be detected by a reduction in number, or reduction in $^3$H-thymidine uptake, of cultured cells treated with an oligonucleotide. Inhibition of cell growth in vivo, e.g., in a patient with cancer, can be detected by any standard method for detecting tumors such as by X-ray or imaging analysis of a tumor size, or by observing a reduction in mutant p53 protein production or in the production of any known cell-specific or tumor marker within a biopsy or tissue sample.

As used herein a cell growth-inhibiting amount of an oligonucleotide for inhibiting cell growth or proliferation in a mammal is about 0.1 μg to about 100 mg per kg of body weight per day and preferably about 0.1 μg to about 10 mg per kg of body weight per day.

Moreover, a cell growth-inhibiting amount of an oligonucleotide for inhibiting in vitro cell proliferation or growth is about 0.1 μM to about 100 μM of the oligonucleotide, and preferably about 1.0 μM to about 50 μM of oligonucleotide.

In a preferred embodiment an oligonucleotide for inhibiting cellular replication according to the methods of the present invention is a deoxyoligonucleotide having 10 to 100 bases. Moreover, oligonucleotides having any one of the sequences of SEQ ID NO:2, SEQ ID NO:3, SEQ ID NO:4, SEQ ID NO:8, SEQ ID NO:9 or SEQ ID NO:12 are especially preferred oligonucleotides for inhibiting cell growth or for preventing and treating cancer.

However, according to the present invention any oligonucleotide having sufficient complementarity to detectably bind to either strand of SEQ ID NO:1, or a portion thereof, can be used to inhibit mammalian cell growth and to prevent or treat cancer.

Complementarity between nucleic acids is the degree to which the bases in one nucleic acid strand can hydrogen bond, or base pair, with the bases in a second nucleic acid strand. Hence, complementarity can sometimes be conveniently described by the percentage, i.e. proportion, of nucleotides which form base pairs between two strands or within a specific region or domain of two strands. For the present invention sufficient complementarity means that a sufficient number of base pairs exists between the subject oligonucleotides and a DNA having the sequence of either strand of SEQ ID No:1 to achieve detectable binding of the oligonucleotide.

Therefore a sufficient number, but not necessarily all, nucleotides in the present oligonucleotides can have hydrogen bonds to a DNA having the sequence of either strand of SEQ ID NO:1. The number of positions which are necessary to provide sufficient complementarity for binding of the subject oligonucleotides, can be detected by standard procedures including known hybridization and melting temperature determination procedures. Moreover, according to the present invention oligonucleotide binding can be detected by observing a decrease in cell proliferation, e.g., by measuring cell number or $^3$H-thymidine uptake. Accordingly the degree of complementarity between an oligonucleotide of the present invention and either strand of SEQ ID NO:1 need not be 100% so long as oligonucleotide binding can be detected. However, it is preferred that the present oligonucleotides have at least about 50% complementarity with either strand of SEQ ID NO:1. In an especially preferred embodiment sufficient complementarity is greater than 70% complementarity with either strand of SEQ ID NO:1.

Moreover, the degree of complementarity that provides detectable binding between the subject oligonucleotides and SEQ ID NO:1, is dependent upon the conditions under which that binding occurs. It is well known that binding between nucleic acid strands depends on factors besides the degree of mismatch between two sequences. Such factors include the GC content of the region, temperature, ionic strength, the presence of formamide and types of counter ions present. The effect that these conditions have upon binding is known to one skilled in the art. Furthermore, conditions are frequently determined by the circumstances of use. For example, the present oligonucleotides are used for inhibiting cell growth, accordingly no formamide will be present and the ionic strength, types of counter ions, and temperature correspond to physiological conditions. Therefore, oligonucleotides of the present invention are preferably selected by testing whether binding can occur to a DNA having SEQ ID NO:1 under physiological salt and temperature conditions when no formamide is present.

A thorough treatment of the qualitative and quantitative considerations involved in establishing binding conditions that allow one skilled in the art to design appropriate oligonucleotides for use under the desired conditions is provided by Beltz et al., 1983, *Methods Enzymol.* 100: 266–285 and by Sambrook et al.(1989, *Molecular Cloning: A Laboratory Manual,* Vols. 1–3, Cold Spring Harbor Press, NY).

Thus for the present invention, one of ordinary skill in the art can readily design a nucleotide sequence for the subject oligonucleotides which exhibits sufficient complementarity to detectably bind to a chromosomal binding site for p53 protein. As used herein "binding" or "stable binding" means that a sufficient amount of the oligonucleotide is bound or hybridized to this site to permit detection of that binding.

Binding between a DNA encoding a chromosomal site for p53 protein and an oligonucleotide can be detected by any procedure known to one skilled in the art, including both functional or physical binding assays.

Binding may be detected functionally by determining whether binding has an observable effect upon cell growth, e.g., by observing a reduced number of cultured cells or a reduced $^3$H-thymidine uptake into cultured cells treated with the present oligonucleotides relative to untreated cells.

Physical methods for detecting binding between complementary strands of DNA or RNA are well known in the art, and include standard Southern and Northern hybridization, light absorption detection, gel shift, DNA footprinting, alkylation interference and related procedures (as provided for example in Sambrook et al.).

According to the present invention oligonucleotides can bind to a chromosomal site by conventional Watson-Crick base pairing or by non-Watson-Crick base pairing.

Watson-Crick base pairing occurs through formation of base pairs between adenine (A) and thymine (T) or uracil (U) or suitable analogs thereof, and through formation of base pairs between guanine (G) and cytosine (C), or suitable analogs thereof. Moreover, Watson-Crick base pairing can occur when oligonucleotide nucleotides are oriented in an opposite, or anti-parallel, 5' to 3' direction relative to nucleotides within a chromosomal site. Binding of an oligonucleotide by Watson-Crick base pairing can be detected or assayed by any known hybridization procedure (Sambrook et al.)

In contrast to Watson-Crick base pairing, non-Watson-Crick hydrogen bonding occurs when oligonucleotide and chromosomal site nucleotides have the same, or parallel, 5' to 3' orientation. Moreover, when the subject oligonucleotides bind by non-Watson-Crick hydrogen bonding the strands of the chromosomal site do not dissociate and a three stranded or triple-helical oligonucleotide-DNA complex forms. Accordingly, in another embodiment the subject oligonucleotides bind by non-Watson-Crick base pairing to form a triple-helical oligonucleotide-DNA complex, for example as provided in Beal et al. (1991 Science 251: 1360–1363), Mahler et al. (1990, Biochemistry 29: 8820–8826), Haner et al. (1990 Biochemistry 29: 9761–9765), Maher et al. (1989, Science 245: 725–730), Hoogsteen (1959, Acta Crystallography 12: 822), Griffin et al. (1989, Science 245: 967–971), Cooney et al. (1988 Science 241: 456–459) or the like.

In a preferred embodiment, non-Watson-Crick binding of the present oligonucleotides occurs through formation of hydrogen bonds between one of the present oligonucleotides and a double-stranded chromosomal DNA site. In an especially preferred embodiment, non-Watson-Crick binding of the present oligonucleotides occurs through formation of hydrogen bonds between an oligonucleotide T and an A within an AT chromosomal site base pair, or between an oligonucleotide C and a G within a GC chromosomal site base pair, to form T-AT and C-GC base triads, respectively.

Binding of an oligonucleotide by non-Watson-Crick hydrogen bonding to form a triple-helix oligonucleotide-DNA complex can be observed or assayed by art recognized procedures. Such procedures can include oligonucleotide-directed affinity cleavage, DNase I footprinting, methylase interference and related procedures (Moser et al. 1987 Science 238: 645; Strobel et al. 1988 J. Am. Chem. Soc. 110: 7927; Cooney et al. 1988 Science 241: 456–459).

Therefore, the skilled artisan can readily utilize the teachings of the present invention to make an oligonucleotide having the necessary structural features to bind a chromosomal site with either Watson-Crick or non-Watson-Crick base pairs.

The present oligonucleotides are single-stranded DNA or RNA having nucleotide bases guanine (G), adenine (A), thymine (T), cytosine (C) or uracil (U), or any nucleotide analog that is capable of hydrogen bonding by either Watson-Crick or non-Watson-Crick hydrogen bonds. Nucleotide analogs include pseudocytidine, isopseudocytidine, 3-aminophenyl-imidazole, 2'-O-methyl-adenosine, 7-deazadenosine, 7-deazaguanosine, 4-acetylcytidine, 5-(carboxy-hydroxylmethyl)-uridine, 2'-O-methylcytidine, 5-carboxymethylaminomethyl-2-thioridine, 5-carboxymethylamino-methyluridine, dihydrouridine, 2'-O-methyluridine, 2'-O-methyl-pseudouridine, beta, D-galactosylqueosine, 2'-O-methylguanosine, inosine, N6-isopentenyladenosine, 1-methyladenosine, 1-methyl-pseudouridine, 1-methylguanosine, 1-methylinosine, 2,2-dimethylguanosine, 2-methyladenosine, 2-methylguanosine, 3-methylcytidine, 5-methylcytidine, 5-methyluridine, N6-methyl-adenosine, 7-methylguanosine, 5-methylamino-methyluridine, 5-methoxyaminomethyl-2-thiouridine, β-D-mannosylqueosine, 5-methoxycarbonylmethyluridine, 5-methoxyuridine, 2-methyl-thio-N6-isopentenyladenosine, N-(9-beta-D-ribofuranosyl-2-methylthiopurine-6-yl)-carbamoyl) threonine, N-(9-beta-D-ribofuranosylpurine-6-yl)-N-methylcarbamoyl)threonine. When possible, either ribose or deoxyribose sugars can be used with these analogs. Nucleotide bases in an α-anomeric conformation can also be used in the oligonucleotides of the present invention.

Preferred nucleotide analogs are unmodified G, A, T, C and U nucleotides; pyrimidine analogs with lower alkyl, lower alkoxy, lower alkylamine, phenyl or lower alkyl substituted phenyl groups in the 5 position of the base and purine analogs with similar groups in the 7 or 8 position of the base. Especially preferred nucleotide analogs are 5-methylcytosine, 5-methyluracil, diaminopurine, and nucleotides with a 2'-O-methylribose moiety in place of ribose or deoxyribose.

As used herein lower alkyl, lower alkoxy and lower alkylamine contain from 1 to 6 carbon atoms and can be straight chain or branched. These groups include methyl, ethyl, propyl, isopropyl, butyl, isobutyl, tertiary butyl, amyl, hexyl and the like. A preferred alkyl group is methyl.

The present oligonucleotides can be made by any of a myriad of procedures known for making DNA or RNA oligonucleotides. For example, such procedures include enzymatic synthesis and chemical synthesis.

Enzymatic methods of DNA oligonucleotide synthesis frequently employ Klenow, T7, T4, Taq or E. coli DNA polymerases as described in Sambrook et al. Enzymatic methods of RNA oligonucleotide synthesis frequently employ SP6, T3 or T7 RNA polymerase and reverse transcriptase as described in Sambrook et al. To prepare oligonucleotides enzymatically requires a template nucleic acid which can either be synthesized chemically, or be obtained as mRNA, genomic DNA, cloned genomic DNA, cloned cDNA or other recombinant DNA. Some enzymatic methods of DNA oligonucleotide synthesis can require an additional primer oligonucleotide which can be synthesized chemically. Finally, oligonucleotides can be prepared by polymerase chain reaction (PCR) techniques as described, for example, by Saiki et al., 1988, *Science* 239:487.

Chemical synthesis of oligonucleotides is well known in the art and can be achieved by solution or solid phase techniques. Moreover, oligonucleotides of defined sequence can be purchased commercially or can be made by any of several different synthetic procedures including the phosphoramidite, phosphite triester, H-phosphonate and phosphotriester methods, typically by automated synthesis methods.

Synthetic oligonucleotides may be purified by polyacrylamide gel electrophoresis, or by any of a number of chromatographic methods, including gel chromatography and high pressure liquid chromatography. To confirm a nucleotide sequence, oligonucleotides may be subjected to DNA sequencing by any of the known procedures, including Maxam and Gilbert sequencing, Sanger sequencing, capillary electrophoresis sequencing the wandering spot sequencing procedure or by using selective chemical degradation of oligonucleotides bound to Hybond paper. Sequences of short oligonucleotides can also be analyzed by plasma desorption mass spectroscopy or by fast atom bombardment (McNeal, et al., 1982, *J. Am. Chem. Soc.* 104: 976; Viari, et al., 1987, *Biomed. Environ. Mass Spectrom.* 14: 83; Grotjahn et al., 1982, *Nuc. Acid Res.* 10: 4671). Sequencing methods are also known in the art for RNA oligonucleotides.

The present invention also contemplates derivatization or chemical modification of the subject oligonucleotides with chemical groups to facilitate cellular uptake. For example, covalent linkage of a cholesterol moiety to an oligonucleotide can improve cellular uptake by 5- to 10-fold which in turn improves DNA binding by about 10-fold (Boutorin et al., 1989, *FEBS Letters* 254: 129–132). Other ligands for cellular receptors may also have utility for improving cellular uptake, including, e.g. insulin, transferrin and others. Similarly, derivatization of oligonucleotides with poly-L-lysine can aid oligonucleotide uptake by cells (Schell, 1974, *Biochem. Biophys. Acta* 340: 323, and Lemaitre et al., 1987, *Proc. Natl. Acad. Sci. USA* 84: 648). Certain protein carriers can also facilitate cellular uptake of oligonucleotides, including, for example, serum albumin, nuclear proteins possessing signals for transport to the nucleus, and viral or bacterial proteins capable of cell membrane penetration. Therefore, protein carriers are useful when associated with or linked to the oligonucleotides of this invention.

Accordingly, the present invention contemplates derivatization of the subject oligonucleotides with groups capable of facilitating cellular uptake, including hydrocarbons and non-polar groups, cholesterol, poly-L-lysine and proteins, as well as other aryl or steroid groups and polycations having analogous beneficial effects, such as phenyl or naphthyl groups, quinoline, anthracene or phenanthracene groups, fatty acids, fatty alcohols and sesquiterpenes, diterpenes and steroids.

In accordance with the present invention, modification in the phosphodiester backbone of oligonucleotides is also contemplated. Such modifications can aid uptake of the oligonucleotide by cells or can extend the biological half-life of such oligonucleotides. For example, oligonucleotides may penetrate the cell membrane more readily if the negative charge on the internucleotide phosphate is eliminated. This can be done by replacing the negatively charged phosphate oxygen with a methyl group, an amine or by changing the phosphodiester linkage into a phosphotriester linkage by addition of an alkyl group to the negatively charged phosphate oxygen. Alternatively, one or more of the phosphate atoms which is part of the normal phosphodiester linkage can be replaced. For example, NH—P, $CH_2$—P or S—P linkages can be formed. Accordingly, the present invention contemplates using methylphosphonates, phosphorothioates, phosphorodithioates, phosphotriesters and phosphorus-boron (Sood et al., 1990, *J. Am. Chem. Soc.* 112: 9000) linkages. The phosphodiester group can be replaced with siloxane, carbonate, acetamidate or thioether groups. These modifications can also increase the resistance of the subject oligonucleotides to nucleases. Methods for synthesis of oligonucleotides with modified phosphodiester linkages are reviewed by Uhlmann et al. (1990, *Chemical Reviews* 90: 543–584).

A further aspect of this invention provides pharmaceutical compositions containing the subject oligonucleotides with a pharmaceutically acceptable carrier. In particular, the subject oligonucleotides are provided in a therapeutically effective amount of about 0.1 μg to about 100 mg per kg of body weight per day, and preferably of about 0.1 μg to about 10 mg per kg of body weight per day, to bind to a nucleic acid in accordance with the methods of this invention. Dosages can be readily determined by one of ordinary skill in the art and formulated into the subject pharmaceutical compositions.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The subject oligonucleotides can be provided to a mammalian cell by topical or parenteral administration, for example, by intraveneous, intramuscular, intraperitoneal, subcutaneous or intradermal route, or when suitably protected, the subject oligonucleotides can be orally administered. The subject oligonucleotides may be incorporated into a cream, solution or suspension for topical administration. For oral administration, oligonucleotides may be protected by enclosure in a gelatin capsule. Oligonucleotides may be incorporated into liposomes or liposomes modified with polyethylene glycol for parenteral administration. Incorporation of additional substances into the liposome, for example, antibodies reactive against membrane proteins found on specific target cells, can help target the oligonucleotides to specific cell types.

Topical administration and parenteral administration in a liposomal carrier is preferred.

The following examples further illustrate the invention.

EXAMPLE 1

Inhibition of Cellular Replication by Oligonucleotides

Oligonucleotides having the following sequences were synthesized by automated DNA synthetic procedures:

```
p53(1) (SEQ ID NO:2):
     1
    5' CTTGCCTGGACTTGCCTGGCCTTGCCTTTTCTTTCTTT;

p53(2) (SEQ ID NO:3):
    5'-AAAGAAAGAAAAGGCAAGGCCAGGCAAGTCCAGGCAAG;

p53(3) (SEQ ID NO:4):
    5'-CTGGCCTTGCCTTTTCTTTCTTTCTTTCTTTCTTTA;

p53(4) (SEQ ID NO:5):
    5'-TAAAGAAAGAAAGAAAGAAAGAAAAGGCAAGGCCAG;

p53(1R) (SEQ ID NO:6):
    5'-CTTGCCTGGACGGTCCGTTCCTTGCCTTTTTTCTTTC;

Hoog1 (SEQ ID NO:8):
    5'-TTTCTTTCTTTCTTTCTTTCTTTTCC;

Hoog2 (SEQ ID NO:9):
    5'-CTTCTTCTTCTTTTTCTCTTTC;

Hoog3 (SEQ ID NO:10):
    5'-CCCTTTTTTCCTTTTTTTCTTTTTCT;

Hoog4 (SEQ ID NO:11):
    5'-TTTCTCTTTTCTTTTCTCCTTC;

Hoog5 (SEQ ID NO:12):
    5'-TTTCTTTCTTTTCCTTTCCTTTCC.
```

Oligonucleotides having SEQ ID NO:2 and SEQ ID NO:4 are complementary to oligonucleotides having SEQ ID NO:3 and SEQ ID NO:5, respectively. Oligonucleotides having SEQ ID NO:2 and 3 correspond to positions 56–83 of SEQ ID NO:1 while oligonucleotides having SEQ ID NO:4 and 5 correspond to positions 61–96 of SEQ ID NO:1. The oligonucleotide having SEQ ID NO:6 (p53(1R)) is a control oligonucleotide having the same size and base composition as SEQ ID NO:2 but with two inversions in nucleotide sequence between bases 11–20 and 31–38, relative to the nucleotide sequence of SEQ ID NO:2.

Oligonucleotides having SEQ ID NO:8 and SEQ ID NO:9 correspond to positions 70–95 and 100–121 of SEQ ID NO:1, respectively. An oligonucleotide having SEQ ID NO:12 has 87.5% homology to a region of SEQ ID NO:1 corresponding to positions 60–83. Oligonucleotides having SEQ ID NO:10 and 11 are controls having the same base composition and length, but a different sequence, than SEQ ID NO:8 and 9, respectively.

Oligonucleotides having SEQ ID NO:2, 3, 4, 5, 8, 9 and 12 were made to bind in a parallel; i.e. non-Watson Crick, manner relative to the bound chromosomal DNA strand.

Oligonucleotides were synthesized on a Milligen 8750 DNA synthesizer using phosphoramidite chemistry by LSUMC Core Laboratories, New Orleans.

Colon adenocarcinoma cells (Colo 201) and primary human mesangial cells (passage 5–6) were maintained in 80% RPMI (Gibco-BRL), 20% fetal bovine serum (FBS) and in 80% RPMI, 10% FBS with ITS supplement, respectively. ITS (Collaborative Research) contains 5 µg/ml insulin, 5 µg/ml transferrin and 5 ng/ml selenious acid. Each cell type was plated at 7000 cells/microtiter well, grown for two days and then serum deprived for one day in media containing 0.5% FBS. Low serum media were removed and replaced with media containing 10% FBS and 10 µM oligonucleotide or vehicle, i.e. a volume of water equivalent to the volume of oligonucleotide solution added. Media and oligonucleotides were replaced every 12 hr for a time period of 48 hr. During the final 24 hr, 10 µCi/ml $^3$H-thymidine (New England Nuclear), was added at each media change. Cells were harvested and bioassays performed using a Tomtec Harvester 96 Mach II and an LKB 1205 Betaplate scintillation counter. Cells in parallel cultures were harvested, stained with trypan blue for viability and counted.

Table 1 depicts the effect of oligonucleotides having SEQ ID NO:2–6 upon cell growth of cultured colon and cultured mesangial cells as observed by cell counting. When cultured colon carcinoma cells are treated with an oligonucleotide having SEQ ID NO:2 or SEQ ID NO:4 cell counts were inhibited by about 50%, relative to control cells receiving no oligonucleotide (vehicle, i.e. water). Similarly, oligonucleotide having SEQ ID NO:2 inhibited cell counts of mesangial cells by about 30%.

Under similar culture conditions, oligonucleotide SEQ ID NO:3 (complementary to SEQ ID NO:2) reduced colon and mesangial cell counts by about 30% and 11% respectively. However, an oligonucleotide having SEQ ID NO:5 with a complementary sequence to SEQ ID NO:4 and a capacity to bind to SEQ ID NO:1, had little effect upon colon cell counts.

Table 2 depicts $^3$H-thymidine incorporation into the DNA of cells cultured with an oligonucleotide having SEQ ID NO:2–6 or without an oligonucleotide (i.e. vehicle). Oligonucleotides having SEQ ID NO:2, SEQ ID NO:3 and SEQ ID NO:4 caused an approximate 50% reduction in $^3$H-thymidine incorporation into colon cells, relative to colon cells receiving no oligonucleotide. In contrast, an oligonucleotide having SEQ ID NO:5 had little or no effect upon cell growth as measured by $^3$H-thymidine incorporation. Moreover, control oligonucleotide SEQ ID NO:6, having the same base composition and a partially inverted sequence relative to SEQ ID NO:2 reduced $^3$H-thymidine incorporation into colon cells by only 17%.

Growth of mesangial cells was less affected than was growth of colon cells by oligonucleotides having SEQ ID NO:2 and 3. However, inhibition of mesangial cell growth by these oligonucleotides was still significant as measured by $^3$H-thymidine incorporation (Table 2). In particular, oligonucleotide SEQ ID NO:2 caused a 22% reduction, and oligonucleotide SEQ ID NO:3 caused a 13% reduction, in $^3$H-thymidine incorporation into mesangial cells.

Oligonucleotides having SEQ ID NO:8, 9 and 12 caused even greater inhibition of cell growth as measured by $^3$H-thymidine incorporation into colon cells (Table 3). In particular, oligonucleotides with SEQ ID NO:9 and 12 caused at least an 85% reduction in cell growth and an oligonucleotide with SEQ ID NO:8 caused at least a 75% reduction in cell growth as measured by $^3$H-thymidine uptake. Control oligonucleotides having SEQ ID NO:10 and 11 caused no reduction in cell growth, and may have even increased cell growth slightly, indicating that the specific sequence of the oligonucleotide is a critical factor effecting cell growth.

TABLE 1

Cell Counts: Colon Carcinoma Cells and Human Mesangial Cells Cultured with Oligonucleotides

| | Colon Carcinoma Cells | | |
|---|---|---|---|
| | SEQ ID NO:2 | SEQ ID NO:3 | Vehicle |
| | 9,200 | 13,000 | 20,100 |
| | 10,300 | 11,200 | 17,700 |
| | 9,700 | 14,800 | 17,500 |
| Mean | 9,733 | 13,000 | 18,433 |

| | Colon Carcinoma Cells | | | |
|---|---|---|---|---|
| | SEQ ID NO:4 | SEQ ID NO:5 | SEQ ID NO:6 | Vehicle |
| | 11,100 | 17,000 | 21,000 | 23,500 |
| | 12,600 | 16,500 | 22,000 | 23,800 |
| | 10,300 | 20,000 | 17,300 | 21,600 |
| Mean | 11,333.3 | 17,833.3 | 20,100 | 22,966.6 |

| | Human Mesangial Cells | | |
|---|---|---|---|
| | SEQ ID NO:2 | SEQ ID NO:3 | Vehicle |
| | 20,000 | 22,500 | 26,000 |
| | 15,000 | 20,150 | 22,000 |
| | 16,000 | 21,600 | 24,200 |
| Mean | 17,000 | 21,417 | 24,067 |

TABLE 2

$^3$-H-Thymidine Incorporation (CPM's) into DNA of Cells Cultured with Oligonucleotides

| | Human Colon Carcinoma Cells | | |
|---|---|---|---|
| | SEQ ID NO:2 | SEQ ID NO:3 | Vehicle |
| | 10,884.7 | 11,908.8 | 20,109.1 |
| | 11,654.2 | 12,346.8 | 19,789.0 |
| | 10,111.8 | 11,994.7 | 21,008.4 |
| | 11,039.6 | 11,853.6 | 18,435.1 |
| | 8,408.1 | 11,198.6 | 18,095.6 |
| | 9,882.7 | 9,497.2 | 19,850.7 |
| Mean | 10,330.2* | 11,466.6* | 19,548 |

*p < 0.01, compared to vehicle (Wilcoxan Rank Sum)

| | Human Colon Carcinoma Cells | | |
|---|---|---|---|
| | SEQ ID NO:2 | SEQ ID NO:6† | Vehicle |
| | 8,641.3 | 14,361.2 | 17,600.9 |
| | 8,996.4 | 14,111.2 | 18,100.6 |
| | 10,002.3 | 15,326.4 | 17,325.2 |
| | 9,959.2 | 15,980.2 | 18,315.2 |
| | 10,054.3 | 14,960.1 | 19,075.2 |
| | 10,157.2 | 15,498.4 | |
| Mean | 9,635.1 | 15,039.6* | 18,083.4* |

*Different from SEQ ID NO:2 (p < 0.01) by Wilcoxan Rank Sum Test
†a partially inverted SEQ ID NO:2 sequence

| | Human Colon Carcinoma Cells | | | |
|---|---|---|---|---|
| | SEQ ID NO:4 | SEQ ID NO:5 | SEQ ID NO:6 | Vehicle |
| | 12,105.2 | 20,417.0 | 16,012.8 | 24,009.5 |
| | 11,824.3 | 20,277.9 | 10,064.9 | 19,156.8 |
| | 8,217.4 | 13,907.1 | 23,793.3 | 22,165.2 |
| Mean | 10,715.6 | 18,200.6 | 19,957.0 | 21,777.2 |

| | Cultured Mesangial Cells | | |
|---|---|---|---|
| | SEQ ID NO:2 | SEQ ID NO:3 | Vehicle |
| | 19,152.6 | 21,664.2 | 25,612.8 |
| | 18,666.4 | 22,000.2 | 24,981.6 |
| | 21,324.8 | 22,321.6 | 24,911.3 |
| Mean | 19,714.6 | 21,995.3 | 25,168.6 |

TABLE 3

Mean $^3$H-Thymidine Incorporation by Colo 201 Cells (in CPM's)

| Vehicle 1 | 16,504.1 | ±2432 |
|---|---|---|
| Vehicle 2 | 16,807.4 | |
| SEQ ID NO:8 | 4,205.0 | ±1840 |
| SEQ ID NO:9 | 2,480.3 | ±686 |
| SEQ ID NO:10 | 18,900.9 | ±2656 |
| SEQ ID NO:11 | 19,152.7 | ±3492 |
| SEQ ID NO:12 | 2,478.8 | ±210 |

EXAMPLE 2

Quantitation of Mutant p53 Protein in Cultured Cells

The quantity of p53 protein in cultured colon carcinoma and human mesangial was determined by an ELISA assay (Oncogene Sciences, New York) which can selectively detect mutant p53 proteins without significantly reacting with wild type p53.

Materials and Methods

Cells were plated and grown to semi-confluence in T-175 tissue culture flasks. Cell extracts were prepared using a non-ionic detergent method to avoid denaturation of p53 proteins since denaturation can cause anti-mutant p53 antibodies to cross-reactive with wild type p53 protein. ELISA determinations were performed in parallel on cell extracts prepared from primary mesangial (MC) cell lines, which were expected to have mostly wild type p53 protein, and from transformed colon carcinoma (Colo 201), cell lines, which were expected to have mostly mutant p53, using kits provided by Oncogene Sciences (New York). Extracts were also measured for protein content using a Bio-Rad protein assay (Bio-Rad Laboratories, Richmond, Calif.).

Results

Table 4 depicts the quantity of mutant p53 protein per unit volume and per mg of total cell protein. As shown, Colo 201 cells possess approximately 12-fold more mutant p53 protein per mg of total cell protein than do mesangial cells. The Colo 201 cell line was obtained from a colon carcinoma. In contrast, the mesangial cells used in this study are a primary cell line derived from normal, non-cancerous human kidney and have normal levels of wild type p53 protein. Furthermore, as shown in Example 1, oligonucleotides having SEQ ID NO:2–5 inhibit cellular proliferation to a greater extent in Colo 201 cells than in mesangial cells. Therefore, even though there is substantially more oncogenic mutant p53 protein in Colo 201 cells, cellular proliferation in Colo 201 cells is inhibited to a greater extent than is cellular proliferation in normal mesangial cells. Accordingly, the present methods can be used to selectively inhibit cellular proliferation in cancerous cells.

TABLE 4

Quantity of Mutant p53 Protein in Cancerous and Non-Cancerous Cells

| Cell Line | Mutant p53 (ng/ml extract) | Mutant p53 (ng/mg protein) |
| --- | --- | --- |
| Colo 201 | 52.5 ± 6.5 | 6.60 |
| Mesangial cells | 0.8 ± 0.2 | 0.53 |

---

What is claimed is:

1. A method for inhibiting the growth of a cancerous mammalian cell, wherein said cell comprises a mutant p53 protein or lacks p53 protein, comprising providing said mammalian cell with a cell growth-inhibiting amount of a DNA oligonucleotide which binds to a chromosomal binding site of wild type p53 protein to form a complex between said oligonucleotide and said binding site, wherein said complex is sufficiently stable to inhibit said mammalian cell growth; and wherein said chromosomal binding site comprises any one of positions 60–83, 70–95, 71–82, 100–121 or 60–121 of SEQ ID NO: 1.

2. The method of claim 1 wherein providing said growing mammalian cell comprises topical or parenteral administration to a mammal.

3. A method for treating cancer caused by a mutation or loss of a p53 gene which comprises administering to a patient a therapeutically effective amount of a DNA oligonucleotide which binds to a chromosomal binding site for a wild type p53 protein to form a complex between said oligonucleotide and said binding site, wherein said complex is sufficiently stable to inhibit cell growth; and wherein said chromosomal binding site comprises any one of position 60–83, 70–95, 71–82 or 100–121 of SEQ ID NO: 1.

4. A method for inhibiting chromosomal replication in a mammalian cell wherein said cell comprises a mutant p53 protein or lacks p53 protein, comprising providing a mammalian cell with a DNA replication-inhibiting amount of a DNA oligonucleotide which binds to a chromosomal binding site for wild type p53 protein to form a complex between said oligonucleotide and said binding site, wherein said complex is sufficiently stable to inhibit chromosomal replication; and wherein said chromosomal binding site comprises positions 60–83, 70–95, 71–82, 100–121 or 60–121 of SEQ ID NO: 1.

5. The method of any one of claims 1, 3, or 4 wherein said chromosomal binding site comprises positions 100–121 of SEQ ID NO: 1.

6. The method of any one of claims 1, 3, or 4 wherein said chromosomal binding site comprises positions 71–82 of SEQ ID NO: 1.

7. The method of claim 1 or 3 which further comprises inhibiting DNA replication at said site.

8. The method of claim 1 wherein said cell is a human, ape, monkey, mouse, rat, hamster, rabbit, cat, dog, horse, sheep, cow or bull cell.

9. The method of claim 1 wherein said cell is an opithelial, mesothelial or endothelial cell.

10. The method of claim 3 wherein said cancer is a carcinomas or a sarcoma.

11. The method of claim 3 wherein said cancer is a cancer in a mesangial, embryonic, brain, lung, breast, uterine, cervical, ovarian, prostate, adrenal cortex, skin, blood, brain, bladder, gastrointestinal or colon cell.

12. The method of claim 3 wherein said cancer is a sarcoma, breast cancer, brain cancer, adrenal cortex cancer, colon cancer, bladder cancer, prostate cancer, lung cancer or leukemic cancer.

13. The method of claim 1 or 3 wherein said oligonucleotide binds to said chromosomal site by non-Watson-Crick base pairs to form a triple-helical oligonucleotide-DNA complex.

14. The method of claim 1 or 3 wherein said oligonucleotide binds to said chromosomal site by Watson-Crick base pairs to form a double helical oligonucleotide-DNA complex.

15. The method of claim 1 or 3 wherein said oligonucleotide comprises adenine or a suitable analog thereof, thymine or a suitable analog thereof, guanine or a suitable analog thereof, cytosine or a suitable analog thereof or uracil or a suitable analog thereof.

16. The method of claim 15 wherein said analog of cytosine is 5-methylcytosine.

17. The method of claim 15 wherein said analog of uracil is 5-methyluracil.

18. The method of claim 15 wherein said analog of adenine is diaminopurine.

19. The method of claim 15 wherein said nucleotides have a 2'-o-methylribose in place of ribose or deoxyribose.

20. The method of claim 1 or 3 wherein said oligonucleotide further comprises a ligand for a cellular receptor, a cholesterol group, an aryl group, a steroid group or a polycation.

21. The method of claim 1 or 3 wherein said oligonucleotide comprises SEQ ID NO: 8, SEQ ID NO: 9, or SEQ ID NO: 12.

22. The method of claim 1 wherein said cell growth-inhibiting amount of said oligonucleotide is about 0.1 $\mu$M to about 100 $\mu$M of said oligonucleotide.

23. The method of claim 22 wherein said cell growth-inhibiting amount of said oligonucleotide is about 1.0 $\mu$M to about 50 $\mu$M of said oligonucleotide.

24. The method of claim 3 wherein said therapeutically effective amount of said oligonucleotide is about 0.1 $\mu$g to about 100 mg per kg of body weight per day.

25. The method of claim 24 wherein said therapeutically effective amount of said oligonucleotide is about 0.1 $\mu$g to about 10 mg per kg of body weight per day.

26. A composition comprising a therapeutically effective amount of an oligonucleotide comprising any one of SEQ ID NO: 8, SEQ ID NO: 9 or SEQ ID NO: 12 and a pharmaceutically acceptable carrier.

27. The composition of claim 26 wherein said oligonucleotide comprises SEQ ID NO: 8, SEQ ID NO: 9 OR SEQ ID NO: 12.

28. The composition of claim 26 wherein said therapeutically effective amount of said oligonucleotide is about 0.1 $\mu$g to about 100 mg per kg of body weight per day.

29. The composition of claim 28 wherein said therapeutically effective amount of said oligonucleotide is about 0.1 µg to about 10 mg per kg of body weight per day.

30. The method of any one of claims 1, 3, or 4 wherein said oligonucleotide has a least about 50% complementary to any one of positions 60–83, 70–95, 71–82 or 100–121 of SEQ ID NO: 1.

31. The method of any one of claims 1, 3, or 4 wherein said oligonucleotide has at least 50% homology to at least one of SEQ ID NO: 8, 9 or 12.

32. The method of any one of claims 1, 3, or 4, wherein said oligonucleotide comprises any one of SEQ ID NO: 8, SEQ ID NO: 9 or SEQ ID NO: 12.

* * * * *

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH: 188 base pairs
      (B) TYPE: nucleic acid
      (C) STRANDEDNESS: both
      (D) TOPOLOGY: linear (ii) MOLECULE TYPE: DNA (genomic)

(xi) SEQUENCE DESCRIPTION: SEQ ID NO: 1:

```
TAAGCTTGAT ATTCTCCCCA GATGTAGTGA AAGCAGGTAG ATTGCCTTGC CTGGACTTGC      60

CTGGCCTTGC CTTTTCTTTC TTTCTTTCTT TCTTTATTAC TTTCTCTTTT TCTTCTTCT      120

CTTCTTCTTC TTCTTCTTCT TCTTCTTCTT CTTCTTCTTC TTCTTCTTCT TTTTTTTTT      180

AGACAGAG                                                              188
```

(2) INFORMATION FOR SEQ ID NO: 2:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 2:

```
CTTGCCTGGA CTTGCCTGGC CTTGCCTTTT CTTTCTTT                              38
```

(2) INFORMATION FOR SEQ ID NO: 3:

(i) SEQUENCE CHARACTERISTICS:
      (A) LENGTH: 38 base pairs
      (B) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO: 3:

AAAGAAAGAA AAGGCAAGGC CAGGCAAGTC CAGGCAAG                                38

(2) INFORMATION FOR SEQ ID NO: 4:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 4:

CTGGCCTTGC CTTTTCTTTC TTTCTTTCTT TCTTTA                                  36

(2) INFORMATION FOR SEQ ID NO: 5:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 5:

TAAAGAAAGA AAGAAAGAAA GAAAAGGCAA GGCCAG                                  36

(2) INFORMATION FOR SEQ ID NO: 6:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 6:

CTTGCCTGGA CGGTCCGTTC CTTGCCTTTT TTTCTTTC                                38

(2) INFORMATION FOR SEQ ID NO: 7:

(i) SEQUENCE CHARACTERISTICS:
            (A) LENGTH: 29 base pairs
            (B) TYPE: nucleic acid
            (C) STRANDEDNESS: both
            (D) TOPOLOGY: linear (ii) MOLECULE TYPE: DNA (genomic)

(xi) SEQUENCE DESCRIPTION: SEQ ID NO: 7:

TGCCTTGCCT GGACTTGCCT GGCCTTGCC                                          29

(2) INFORMATION FOR SEQ ID NO: 8:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 8:

TTTCTTTCTT TCTTTCTTTC TTTTCC                                    26

(2) INFORMATION FOR SEQ ID NO: 9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

CTTCTTCTTC TTTTTCTCTT TC                                        22

(2) INFORMATION FOR SEQ ID NO: 10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

CCCTTTTTTC CTTTTTTTCT TTTTCT                                    26

(2) INFORMATION FOR SEQ ID NO: 11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

TTTCTCTTTT CTTTTCTCCT TC                                        22

(2) INFORMATION FOR SEQ ID NO: 12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

TTTCTTTCTT TTCCTTTCCT TTCC                                      24

(2) INFORMATION FOR SEQ ID NO: 13:

(i) SEQUENCE CHARACTERISTICS:
        (A) LENGTH: 24 base pairs
        (B) TYPE: nucleic acid
        (C) STRANDEDNESS: double
        (D) TOPOLOGY: linear -continued (ii) MOLECULE TYPE: DNA (genomic)

(xi) SEQUENCE DESCRIPTION: SEQ ID NO: 13:

TTTCTTTCTT TTCCGTTCCG GTCC                                    24